United States Patent
Pattikonda et al.

(10) Patent No.: US 7,039,228 B1
(45) Date of Patent: May 2, 2006

(54) SYSTEM AND METHOD FOR THREE-DIMENSIONAL SURFACE INSPECTION

(75) Inventors: Ramakrishna Pattikonda, Dallas, TX (US); Youling Lin, Plano, TX (US)

(73) Assignee: Rudolph Technologies, Inc., Flanders, NJ (US)

( * ) Notice: Subject to any disclaimer, the term of this patent is extended or adjusted under 35 U.S.C. 154(b) by 0 days.

(21) Appl. No.: 09/444,034

(22) Filed: Nov. 19, 1999

(51) Int. Cl.
*G06K 9/00* (2006.01)

(52) U.S. Cl. ...................... 382/145; 382/165; 356/603; 348/87

(58) Field of Classification Search ................ 382/147, 382/154, 144–146, 286, 165; 348/87, 126, 348/128, 221.1, 132; 356/630, 631, 603, 356/606, 607; 250/559.27
See application file for complete search history.

(56) References Cited

U.S. PATENT DOCUMENTS

| | | | | |
|---|---|---|---|---|
| 3,187,185 A | * | 6/1965 | Milnes | 250/222.1 |
| 4,253,113 A | * | 2/1981 | Decavel et al. | 250/559.39 |
| 4,767,212 A | * | 8/1988 | Kitahashi et al. | 356/627 |
| 4,803,371 A | * | 2/1989 | Durland | 250/559.2 |
| 5,055,667 A | * | 10/1991 | Sayag | 348/296 |
| 5,298,977 A | * | 3/1994 | Shintani et al. | 356/631 |
| 5,414,268 A | * | 5/1995 | McGee | 250/559.26 |
| 5,495,337 A | * | 2/1996 | Goshorn et al. | 356/601 |
| 5,555,090 A | * | 9/1996 | Schmutz | 356/601 |
| 6,064,478 A | * | 5/2000 | Paul et al. | 356/237.1 |

* cited by examiner

*Primary Examiner*—Vikkram Bali
*Assistant Examiner*—Colin LaRose
(74) *Attorney, Agent, or Firm*—Slater & Matsil, L.L.P.

(57) ABSTRACT

An optical inspection system and method for inspecting a component on a printed circuit board (PCB) which determines three-dimensional information in a single scan. A first visual light source illuminates the PCB surface and component with a green light while a second visual light source illuminates the PCB and component with a blue light. At least one laser light source simultaneously illuminates the surface of the PCB with a narrow coherent red-light laser beam. The laser light source is mounted off vertical on a movable mount which enables the laser beam to be directed over an area of interest on the surface of the PCB. The system also includes a color scan camera mounted vertically above the PCB. The camera has red, green, and blue channels. The green and blue channels capture an image of the illuminated surface of the PCB which is used by a computer to determine two-dimensional information about the component. The red channel captures a path of the laser beam as it strikes the surface of the PCB and the component. The computer uses the path to determine height information for the component.

6 Claims, 3 Drawing Sheets

SYSTEM AND METHOD FOR THREE-DIMENSIONAL SURFACE INSPECTION

BACKGROUND OF THE INVENTION

1. Technical Field of the Invention

The present invention relates to the inspection of structures on an object and, more specifically, to a system and method for optically obtaining three-dimensional information regarding the position of structures on the surface of an object at high speeds.

2. Description of Related Art

Optical inspection devices typically hold an object to be inspected under an overhead camera, and illuminate the object from a single or multiple light sources. Typically, the optical inspection device lights the object from several directions in order to fully illuminate the surface and any objects thereon. The overhead camera captures a two-dimensional gray-scale (black-and-white) image of the object and structures. In a process commonly called convolution, this image is then sent to a computer which compares the image, pixel by pixel, to a stored image of an object with properly positioned structures thereon. If any differences between the captured image and the image of the object with properly positioned structures are detected, the computer has detected a defective object. A typical application of this inspection technology is in the inspection of printed circuit boards (PCBs).

Other techniques for optical inspection such as the generation of structure grammar from captured images, tracing of structures to produce a set of primitives for the structure edges, the use of alignment techniques utilizing histograms to compensate for vibration and wobble of the support mechanism, and methods of automatic defect classification are disclosed in co-owned U.S. Pat. No. 6,487,307 entitled *System and Method of Optically Inspecting Structures on an Object*, and co-owned U.S. Pat. No. 6,292,260 entitled *System and Method of Optically Inspecting Surface Structures on an Object*, both of which are hereby incorporated by reference herein in their entireties.

Existing optical inspection systems d methods are becoming very efficient at obtaining and analyzing surface structures and defects which reveal themselves in the two dimensions of the surface of the object. However, there is still a problem in rapidly and efficiently obtaining detailed and accurate information about the height of the structures. Some prior art systems have used lasers to obtain height information. When a laser is pointed at a particular point on the surface of the object, a small dot is formed by the laser beam. If the angle of incidence of the laser beam is less than 90 degrees, and there is a structure at this point, the dot is displaced horizontally from the position where the dot would be if there was no structure. The taller the structure, the greater the displacement. The vertically mounted camera can then detect the displacement of the laser dot, and height information can be computed from the magnitude of the displacement in a process known as triangular then. However, this is a slow and inefficient process which is not suitable for obtaining height information over the entire surface of the object.

In order to overcome the disadvantage of existing solutions, it would be advantageous to have a system and method of rapidly and efficiently obtaining three-dimensional information regarding the position of structures on the surface of an object. The present invention provides such a system and method.

SUMMARY OF THE INVENTION

In one aspect, the present invention is an optical inspection system for inspecting at least one structure on a surface of an object. The system includes a first visual light source which illuminates the surface of the object and the structure with a light at a first visual frequency, and a first coherent light source which illuminates the surface of the object with a narrow coherent laser beam simultaneously with for example illumination by the first visual light source. The coherent light beam is emitted at a second visual frequency that is different from the first visual frequency of the visual light source. The first coherent light source is mounted off vertical on a movable mount which enables the coherent light beam to be directed over an area of interest on the surface of the object. The system also includes a color scan camera mounted vertically above the object. The camera has a first channel which captures an image of the illuminated surface of the object and the structure at the first visual frequency, and a second channel which captures a path of the coherent light beam as it strikes the surface of the object and the structure at the second visual frequency. A computer then determines two-dimensional structure information from the image at the first visual frequency, and determines height information for the structure from the path of the coherent light beam at the second visual frequency. The system may also include a second visual light source mounted on an opposite side of the object and illuminating the object at a third visual frequency. Additionally, the system may include a second coherent light source oriented 90 degrees from the first coherent light source.

In another aspect, the present invention is a method of inspecting at least one structure on a surface of an object. The method includes the steps of illuminating the surface of the object and the structure with a first visual light at a first visual frequency, and simultaneously illuminating the surface of the object with a first narrow coherent laser beam at a second visual frequency that is different from the first visual frequency. The first laser beam strikes the surface of the object at an angle of incidence less than 90 degrees. The laser beam is directed in a path covering an area of interest on the surface of the object. This is followed by capturing an image of the illuminated surface of the object and the structure at the first visual frequency utilizing a first channel of a color scan camera mounted vertically above the object. Simultaneously, the path of the laser beam at the second visual frequency is captured utilizing a second channel of the color scan camera as the laser beam strikes the surface of the object and the structure. Two-dimensional structure information is then determined from the image at the first visual frequency, and height information for the structure is determined from the path of the laser beam at the second visual frequency.

BRIEF DESCRIPTION OF THE DRAWINGS

The invention will be better understood and its numerous objects and advantages will become more apparent to those skilled in the art by reference to the following drawings, in conjunction with the accompanying specification, in which.

DETAILED DESCRIPTION OF EMBODIMENTS

The present invention advantageously combines several new inspection techniques in order to rapidly and efficiently obtain three-dimensional information regarding the position of structures on the surface of an object. The exemplary embodiment described herein is discussed in the context of a PCB inspection system. However, the system and method described herein may also be utilized to inspect other types of structures and objects.

Figure 1:
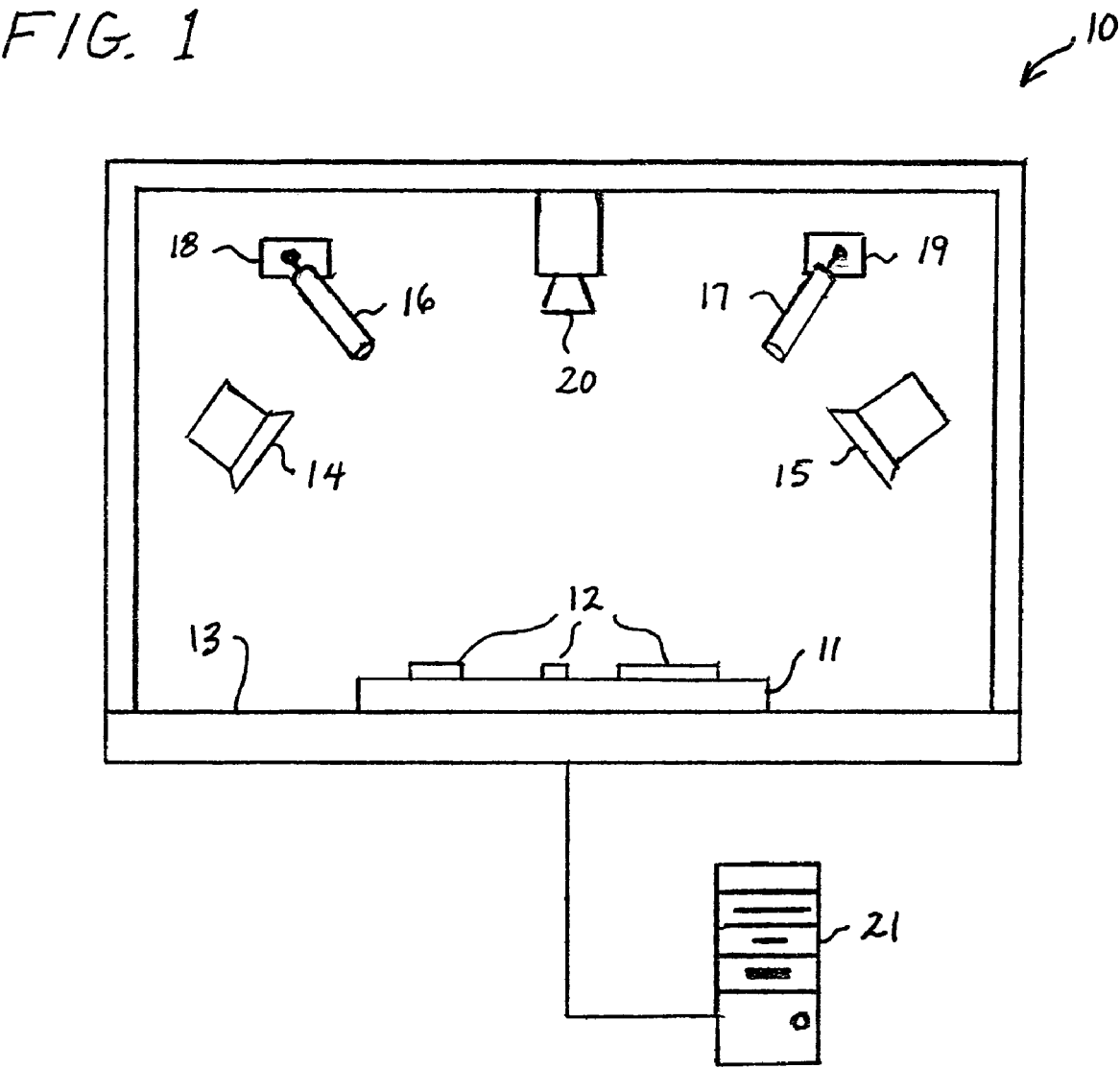
FIG. 1 is a simplified block diagram of a three-dimensional optical inspection system.

FIG. 1 is a simplified block diagram of a three-dimensional optical inspection system 10. The present invention utilizes a coherent light source such as a laser light and multi-spectrum visual light together at the same time. A PCB 11 with components 12, or other formations such as solder blocks, on its surface is supported on a support mechanism 13. Two multi-spectrum visual lights 14 and 15 illuminate the PCB from opposite sides. Light 14 may be, for example green, while light 15 is blue. Two coherent red-light lasers 16 and 17 are mounted off the vertical (i.e., the angle of incidence of their laser beams is less than 90 degrees), and are mounted approximately 90 degrees apart horizontally. Thus, if laser 16 points at the PCB from the front, laser 17 may point at the PCB from the right side or the left side. The lasers are mounted on movable mounts 18 and 19, enabling the lasers to be pointed at any point on the PCB surface. Optics may be used to form line patterns on the surface. Obviously, other colors of lights may be utilized so long as the multi-spectrum visual lights and the laser lights are different colors. The line patterns may also be formed by light sources other than lasers. For example, coherent LED beams may be utilized, or non-coherent lights may be utilized at high angles of incidence in conjunction with color filters, pattern grids, and optical focusing.

A camera 20 is mounted above the PCB surface. The camera performs a high speed scan (that is, a sweep or survey) of the PCB surface and utilizes red, green, and blue (RGB) channels to separate the signals of the laser light and the multi-spectrum visual lights. Camera 20 may be, for example, a multi-channel color-scan camera.

The inspection system is under the control of a control computer 21. The control computer, or another dedicated computer, may also generate structure grammar from captured images, trace structures to produce sets of primitives for the structure edges, align multiple images utilizing histograms to compensate for vibration and wobble of the support mechanism, perform height calculations, and perform automatic defect classification.

In operation, the green light 14 and the blue light 15 are used to illuminate the entire surface of the PCB. Simultaneously, the two coherent red-light lasers 16 and 17 are used to generate a series of parallel lines over the surface of the PCB 11. The lasers are mounted at 90 degree positions from each other and generate a grid of perpendicular red lines on the PCB surface. In addition, the lasers are strobed at a predetermined rate, so that both time-multiplexing and color-multiplexing can be used to separate the laser signal from the visual light signals generated by the green light and the blue light. The camera utilizes its red, green, and blue channels to separate the red, green, and blue signals from the various light sources.

The camera 20 is controlled to point at the same position as one or both of the lasers. Then the camera and the laser are scanned (that is, moved) together over the surface of the PCB and take height readings across the PCB. By using the laser-grid lines, the present invention can obtain height information over the entire surface of the PCB in a single high-speed scan. When a laser grid line encounters an object on the surface of the PCB, there is a discontinuity in the laser grid line. The magnitude of the discontinuity is measured in order to determine the height of the object.

The camera takes a continuous series of exposures as it scans. By controlling the exposure time, the resolution of the height information in the direction of the laser line is controlled. A very short exposure time provides a height reading for a desired point on the surface. A rapid series of short exposures provides a height profile over a region of the surface. For longer exposure times, a series of height measurements may be integrated to provide an average height over the entire surface or a region thereof. By adjusting the exposure time to the spacing between parallel lines, height information over an entire area of the object can be rapidly obtained.

Figure 2:
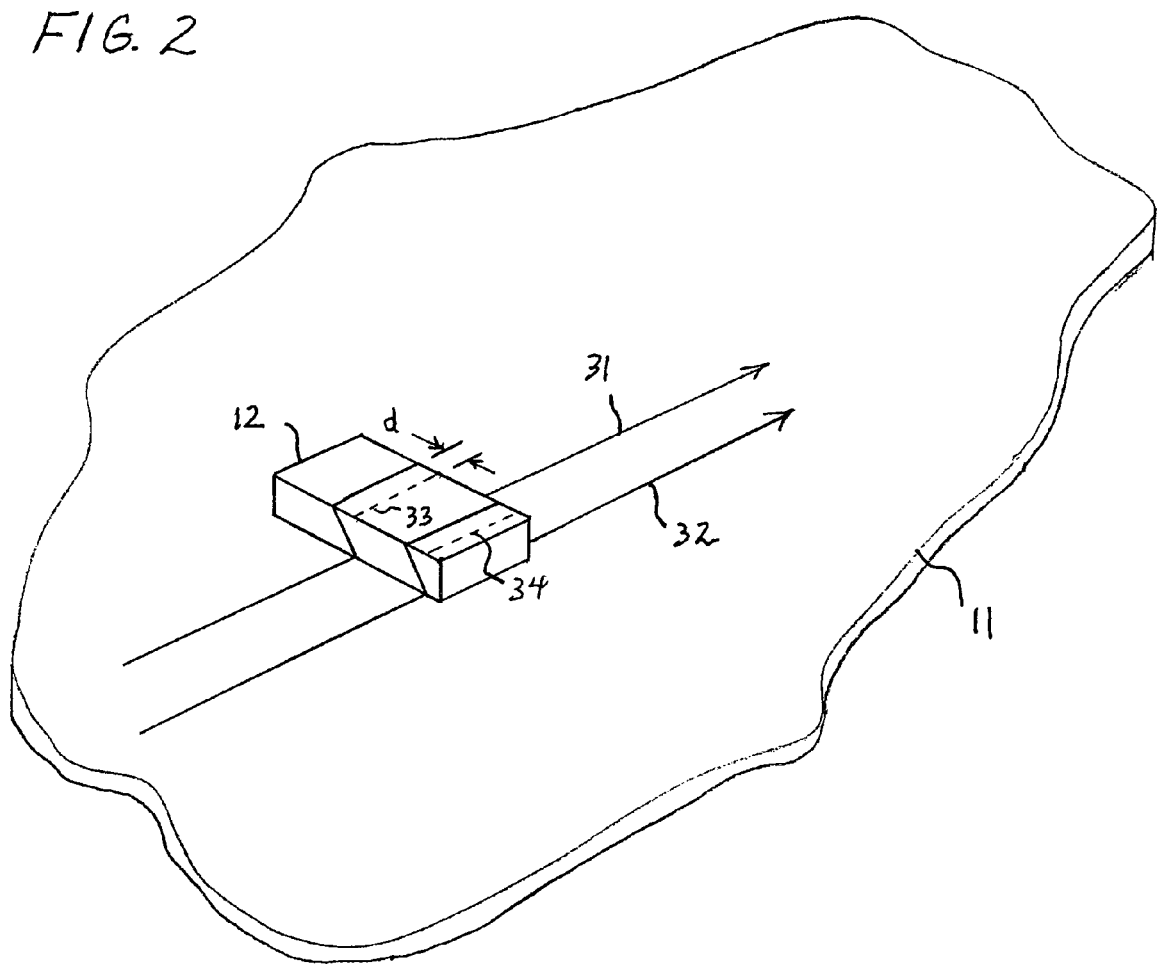
FIG. 2 is an illustrative drawing of a component mounted on the surface of a printed circuit board (PCB) illustrating the height-measurement technique of the present invention.

FIG. 2 is an illustrative drawing of a component 12 mounted on the surface of the PCB 11 illustrating the height-measurement technique of the present invention. Portions of two laser lines 31 and 32 are shown as they cross over the component 12. Dotted lines 33 and 34 illustrate the imaginary positions that lines 31 and 32 would present to the camera 20 if the structure was not present. Lines 31 and 32 are displaced from dotted lines 33 and 34 by distance "d". The displacement distance is dependent on the height of the structure and the angle by which the laser is mounted off the vertical. When the laser is mounted farther off the vertical, smaller height differences cause a greater displacement. Therefore, smaller height differences can be detected.

Figure 3:
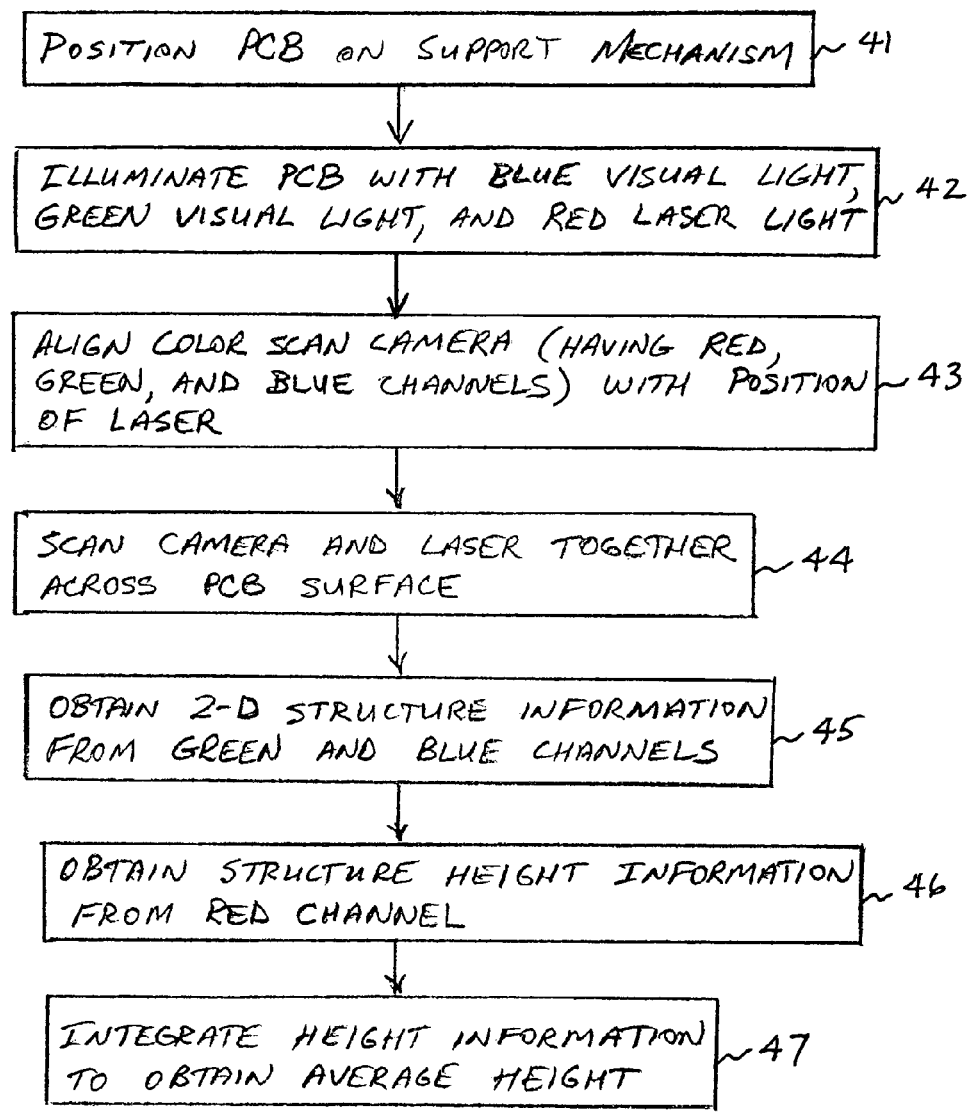
FIG. 3 is a flow chart illustrating the steps of the method of the present invention.

FIG. 3 is a flow chart illustrating the steps of the method of the present invention. At step 41, the PCB 11 to be inspected is positioned on the support mechanism 13. At step 42, the PCB is illuminated with blue visual light, green visual light, and red laser light. At step 43, the camera 20 is aligned with the position of one of the lasers 16 and 17. The camera and the laser are then scanned, (that is, moved or directed) together across the surface of the PCB at 44. The camera uses its red, green, and blue channels to separate the signals from the three light sources. The red signal may be further differentiated, as noted above, by strobing the laser and using time-multiplexing to extract the signal. At 45, the signals from the green and blue channels are analyzed using known techniques to obtain two-dimensional information regarding the structure of the component mounted on the PCB. At 46, the signal from the red channel is analyzed using the techniques illustrated in FIG. 2 to obtain height information for the component. As noted above, this information may be utilized to determine a height profile, or the information may be integrated over a period of time at step 47 to obtain an average height value.

By utilizing the method of the present invention, the present invention can obtain three-dimensional structure information over the entire surface of the PCB in a single high-speed scan.

It is thus believed that the operation and construction of the present invention will be apparent from the foregoing description. While the system and method shown and described has been characterized as being preferred, it will be readily apparent that various changes and modifications could be made therein without departing from the scope of the invention as defined in the following claims.

What is claimed is:

1. A method of inspecting a structure-bearing surface of an object, said method comprising the steps of:

simultaneously forming a plurality of lines on the surface using light emitted from at least one coherent light source at a first wavelength and strobed at a predetermined exposure time;

moving the lines with respect to the surface;

capturing an image of the lines as they move with respect to the surface;

determining height information for structures on the surface from the image of the lines;

illuminating the surface of the object with visible light at a second wavelength, the second wavelength being different from the first wavelength;

capturing a second image of the surface illuminated by the visible light at a second wavelength;

determining two-dimensional information for any surface structures by analyzing the second image;

illuminating the surface with visible light at a third wavelength, the third wavelength being different from the first and second wavelength;

capturing a third image created by the visible light at the third wavelength; and determining two-dimensional information for any surface by analyzing the third image;

wherein the image capturing steps are performed by a camera operable to capture separate images corresponding to light of the first wavelength and of the second wavelength.

2. The method of claim 1, wherein the plurality of lines form a grid on the surface of the object.

3. The method of claim 1, wherein the visible light at a second wavelength is emitted by a visible light source that is strobed at a second predetermined exposure time.

4. The method of claim 3, where in the predetermined exposure time for the coherent light source and the second predetermined exposure time for the visible light source are different.

5. The method of claim 1, wherein the two-dimensional information is combined with the height information to create a profile of structures on the surface of the object.

6. The method of claim 1, wherein the height information is determined by integrating a series of height measurements to provide an average height.

* * * * *